(12) United States Patent
Sanoner et al.

(10) Patent No.: US 10,092,539 B2
(45) Date of Patent: Oct. 9, 2018

(54) CRANBERRY EXTRACT USEFUL IN THE TREATMENT AND PREVENTION OF URINARY INFECTIONS

(71) Applicant: Diana Naturals, Antrain (FR)

(72) Inventors: Philippe Sanoner, Torigny sur Vire (FR); Valerie Bochard, Le Ferre (FR); Lucie Charissou, Fougeres (FR); Benedicte Lastique, Hede (FR); Morgane Jacob, Liffre (FR); Patrice Thomas, Saint Medard sur Ille (FR)

(73) Assignee: Diana Naturals (FR)

( * ) Notice: Subject to any disclaimer, the term of this patent is extended or adjusted under 35 U.S.C. 154(b) by 0 days.

(21) Appl. No.: 14/405,931

(22) PCT Filed: Jun. 7, 2013

(86) PCT No.: PCT/EP2013/061852
§ 371 (c)(1),
(2) Date: Dec. 5, 2014

(87) PCT Pub. No.: WO2013/182702
PCT Pub. Date: Dec. 12, 2013

(65) Prior Publication Data
US 2015/0126598 A1 May 7, 2015

(30) Foreign Application Priority Data

Jun. 7, 2012 (FR) ..................... 12 55324

(51) Int. Cl.
| | |
|---|---|
| A61K 31/191 | (2006.01) |
| A61K 31/353 | (2006.01) |
| A61K 36/45 | (2006.01) |
| A61K 31/194 | (2006.01) |
| A61K 31/192 | (2006.01) |
| C12P 7/46 | (2006.01) |
| C12P 7/42 | (2006.01) |
| C12P 7/48 | (2006.01) |
| C12P 7/40 | (2006.01) |
| C12P 17/06 | (2006.01) |
| A23L 33/105 | (2016.01) |

(52) U.S. Cl.
CPC .......... *A61K 31/353* (2013.01); *A23L 33/105* (2016.08); *A61K 31/191* (2013.01); *A61K 31/192* (2013.01); *A61K 31/194* (2013.01); *A61K 36/45* (2013.01); *C12P 7/40* (2013.01); *C12P 7/42* (2013.01); *C12P 7/46* (2013.01); *C12P 7/48* (2013.01); *C12P 17/06* (2013.01); *A23V 2002/00* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 6,428,837 B1* | 8/2002 | Luzio | A23L 1/0524 426/50 |
| 2008/0020094 A1* | 1/2008 | Lager | 426/50 |
| 2010/0028468 A1 | 2/2010 | Pacioretty et al. | |

FOREIGN PATENT DOCUMENTS

| | | |
|---|---|---|
| EP | 0752871 A1 | 1/1997 |
| EP | 1014969 A1 | 7/2000 |
| EP | 2033641 A1 | 3/2009 |
| EP | 2108268 A1 | 10/2009 |
| WO | 96/30033 A1 | 10/1996 |
| WO | 2010121203 A1 | 10/2010 |

OTHER PUBLICATIONS

Seeram et al., Total Cranberry Extract versus Its Phytochemical Constituents: Antiproliferative and Synergistic Effects against Human Tumor Cell Lines, 2004, J Agric Food Chem, 52: 2512-2517.*

Appeldoorn, M. M., Vincken, J. P., Gruppen, H., and Hollman, P. C. (2009) Procyanidin dimers A1, A2, and B2 are absorbed without conjugation or methylation from the small intestine of rats, J Nutr 139, 1469-1473.

Bazzocco, S.; Mattila, I., Guyot, S.; Renard, C.M.G.C.; Aura, A-M. Factors affecting the conversion of apple polyphenols to phenolic acids and fruit matrix to short-chain fatty acids by human faecal microbiota in vitro. European Daynal of Nutrition vol. 47 issue 8 Dec. 2008. p. 442-452.

Cong, D., Fong, A. K., Lee, R., and Pang, K. S. (2001) Absorption of benzoic acid in segmental regions of the vascularly perfused rat small intestine preparation, Drug Metab Dispos 29, 1539-1547.

Gu, L., Kelm, M., Hammerstone, J. F., Beecher, G., Cunningham, D., Vannozzi, S., and Prior, R. L. (2002) Fractionation of polymeric procyanidins from lowbush blueberry and quantification of procyanidins in selected foods with an optimized normal-phase HPLC-MS fluorescent detection process, J Agric Food Chem 50, 4852-4860.

Sanchez-Patan, F., Bartolome, B., Martin-Alvarez, P. J., Anderson, M., Howell, A., and Monagas, M. (2012) Comprehensive assessment of the quality of commercial cranberry products. Phenolic characterization and in vitro bioactivity, J Agric Food Chem 60, 3396-3408.

Shigemura K, Tanaka K, Okada H, Nakano Y, Kinoshita S, Gotoh A, Arakawa S, Fujisawa M. Pathogen occurrence and antimicrobial susceptibility of urinary tract infection cases during a 20-year period (1983-2002) at a single institution in Japan. Jpn J Infect Dis. Oct. 2005;58(5):303-8.

International Preliminary Report on Patentability issued in corresponding International Application PCT/EP2013/061852, dated May 15, 2014.

* cited by examiner

*Primary Examiner* — Terry A McKelvey
*Assistant Examiner* — Catheryne Chen
(74) *Attorney, Agent, or Firm* — Banner & Witcoff, Ltd.

(57) ABSTRACT

The present invention relates to a concentrated extract of cranberry (*Vaccinium macrocarpon*), the complex composition of which makes it possible to increase the antibacterial effects thereof, which is of use for the prevention or treatment of urinary infections, and in particular for the preventive treatment of urinary infections or treatment against the recurrence thereof. The invention also relates to a process for preparing such an extract, to food, nutraceutical or pharmaceutical compositions comprising the extract and to the use thereof in the treatment or prevention of urinary infections.

16 Claims, 5 Drawing Sheets

Figure 6

CRANBERRY EXTRACT USEFUL IN THE TREATMENT AND PREVENTION OF URINARY INFECTIONS

RELATED APPLICATION DATA

This application is a National Stage Application under 35 U.S.C. 371 of co-pending PCT application PCT/EP2013/061852 designating the United States and filed Jun. 7, 2013; which claims the benefit of FR application number 1255324 and filed Jun. 7, 2012 each of which are hereby incorporated by reference in their entireties.

FIELD OF THE INVENTION

The present invention relates to a concentrated extract of cranberry (*Vaccinium macrocarpon*), the complex composition of which makes it possible to increase its antibacterial effects, which is useful for the prevention or treatment of urinary tract infections, and in particular for the preventive treatment of urinary tract infections or treatment against the recurrence thereof. The invention also relates to a process for preparing such an extract, to food, nutraceutical or pharmaceutical compositions comprising the extract, and to use thereof in the treatment or prevention of urinary tract infections.

PRIOR ART

Urinary tract infections (UTIs) are among the most common infectious diseases, and account for considerable healthcare outlays for society. Microorganisms can reach the urinary tract by a hematogenous or a lymphatic route, but most clinical and experimental evidence shows that ascension of the urethra by microorganisms constitutes the most common route leading to urinary tract infection, in particular by enteric organisms (*Escherichia coli* and other enterobacteria). This provides a logical explanation for the greater frequency of urinary tract infections in women compared to men and for the increased risk of infection following bladder catheterization or instrumentation.

Based on the traditional use of cranberry (*Vaccinium macrocarpon*, also called "American cranberry" or "large cranberry", or "atoca" or "ataca" in Quebec, or "canneberge", "canneberge d'Amérique" or "grande airelle rouge d'Amérique" in French), numerous ingredients arising from the fruit or juice are used in the dietary supplement market as a curative or preventive agent for limiting the risk of urinary tract infections. Epidemiological and clinical links between the consumption of American cranberry and the appearance of urinary tract infections have been shown.

Cranberry is a small (no more than 30 cm) shrub which grows spontaneously only in eastern North America from Carolinas to Canada. It is found in acidic bogs. The fruit is a small berry measuring 10 to 20 mm in diameter. When ripe, it is bright red in color and is acidulous and astringent in flavor.

The berry of cranberry is characterized by its abundance in flavonoids and comprises many different types of compounds, including:
Organic acids, and in particular quinic acid, citric acid and malic acid, and phenolic acids such as benzoic, hydroxy-benzoic and hydroxy-cinnamic acids,
Anthocyans (also called "anthocyanosides"),
Flavanols, and in particular:
Flavan-3-ol monomers such as catechin, epicatechin, gallocatechin and epigallocatechin,
Flavan-3-ol polymers, proanthocyanidins (also called "condensed tannins", or in French "proanthocyanidols" or "proanthocyanidines"),
Gallotannins and ellagitannins (also called hydrolysable tannins),
Flavonols, such as quercetin for example, in glycosylated and/or aglycone form.

Cranberry comprises various organic acids, such as quinic acid, citric acid and malic acid. For a long time, the effect of the consumption of cranberry juice was regarded as related to acidification of the urine, thus limiting the growth of uropathogenic bacteria by decreasing urinary pH.

For example, US2010/028468 describes a composition for treating urinary tract infections, comprising a thymoquinone formulation and cranberry fruits, juice or extracts. The cranberry extract that can be used is a 5:1 extract standardized to contain a quinic acid content of 3.4% (the remainder of its composition is not specified). However, it is mentioned in the introduction that the therapeutic efficacy of cranberry extracts for treating urinary tract infections was not shown.

Indeed, the mechanism of action involving acidification of the urine is too simplified, since in reality these organic acids are metabolized in vivo and thus do not reach the urinary tract intact. Thus, although human cells do not metabolize quinic acid, enzymatic systems of intestinal flora reduce quinic acid into benzoic acid in the colon.

Among organic acids, cranberry is particularly concentrated in various phenolic acids including benzoic, hydroxy-benzoic and hydroxy-cinnamic acids. It thus contains 0.05 g/100 g of hydroxy-benzoic acid (mainly represented by benzoic acid), and less than 0.1 g/100 g of hydroxycinnamic acids, represented mainly by p-coumaric, sinapic and caffeic acids. It also comprises other organic acids than phenolic acids, and in particular quinic acid, which is an intermediate in the synthesis of the benzene nucleus via the shikimate (4-hydroxybenzoic) pathway, which allows the synthesis of aromatic amino acids, phenylpropanoids and phenolic compounds such as hydroxycinnamic acids and flavonoids.

Phenolic acids, and more particularly the most non-polar phenolic acids (such as benzoic acid), disrupt possible metabolic exchanges of bacterial membrane transporters and thus have a bactericidal effect.

However, phenolic acids are bioavailable and easily transported through the intestinal barrier of the small intestine via carboxylate transporters (Cong et al., 2001) and, once in enterohepatic circulation, are then conjugated with glycine to form hippuric acid, finally to be excreted in the urine by the kidneys. The bactericidal activity of hippuric acid is lower than that of phenolic acids. The antibacterial activity provided directly by the phenolic acids of cranberry is thus, in this case, potentially decreased by their bioavailability in the small intestine.

Consequently, the effects of organic acids such as quinic acid and phenolic acids on the prevention or the reduction of the occurrence of urinary tract infections are not completely clear.

For several years, the interest in cranberry for preventing urinary tract infections has been focused on compounds of the proanthocyanidin type (also called "condensed tannins" or "proanthocyanidols", abbreviated as "PAC" in the present description).

PACs are polymers of flavanol units (such as catechin, epicatechin, gallocatechin and epigallocatechin), which can be bound together in various ways.

In particular, two types of bonds have been described:
Type A bonds, in which the two flavanol units are bound by two covalent bonds, one between the C-4 carbon of the first flavanol unit and the C-8 carbon of the second flavanol unit (C-4→C-8), the other being an ether bond between the C-2 carbon of the first flavanol unit and the C-7 carbon of the second flavanol unit (C-2→O→C-7). The presence of PACs with this type of bond is one of the characteristics of cranberry, as few plants have PACs with this type of bond.

Type B bonds, in which the two flavanol units are bound by a single covalent bond, between the C-4 carbon of the first flavanol unit and the C-6 or C-8 carbon of the second flavanol unit (C-4→C-6 or C-4→C-8 bond). These bonds are also present in cranberry PACs.

Cranberry PACs having both type A and type B bonds are particularly polymerized, with a mean degree of polymerization of 15 units in the fruit (Gu et al., 2002), i.e., 80% of the proanthocyanidins having a degree of polymerization greater than 5 and comprising 46% of type A interflavan bonds.

The interest in cranberry PACs comes from the fact that it has been shown in vitro that, like most tannins, these compounds are able to interact with the walls of cells of the urinary tract and/or with the extracellular components of bacteria, limiting their possible interactions and thus potentially the binding or adhesion of bacteria to the walls of the urinary tract. This tanning effect is thus assumed to explain an effect on the appearance and persistence of uropathogenic bacteria colonizing the urinary tract.

For example, patent EP0752871B1 describes extracts of a plant of the genus *Vaccinium* (in particular cranberry) enriched in a fraction having anti-adhesion effects on bacteria and lacking simple or dimeric sugars, acids and anthocyans, purified by chromatography, in particular using a lipophilic column. The fraction having anti-adhesion effects on bacteria corresponds mainly to PACs.

Similarly, application WO96/30033 describes particular PACs having a degree of polymerization between 2 and 18 and use thereof for preventing or treating urinary tract infections via an anti-adhesion effect on bacteria. These PACs are able to be purified from cranberry (see Example I), by a process comprising the alkalization of cranberry at a pH greater than 10 to ionize the phenol groups of polyphenolic compounds into phenoxide groups, precipitation with methanol, re-acidification of the product obtained to reconvert the phenoxide groups into phenols, and purification on a lipophilic column. The obtained extract comprises PACs and flavonoids. In view of the preparation process (use of a lipophilic column in particular), this extract does not comprise significant quantities of organic acids, such as quinic acid or phenolic acids (but only perhaps small residual quantities, largely less than 5% by weight in relation to the total weight of the dry extract).

Patent EP1014969B1 describes a plant (in particular cranberry) PAC extract having an effect of inhibiting adhesion of particular bacteria to surfaces. Said extract containing one or more proanthocyanidins with 5 to 6 units, of which at least two are linked by a type A bond. This extract may be obtained by a process comprising extraction with aqueous solvent, a purification step using chromatography with a lipophilic column or extraction with non-polar solvent, and a second purification step using chromatography with a hydrophilic-lipophilic column. The obtained extract comprises PACS, but it lacks in particular sugars, organic acids, anthocyans and flavonols.

Application EP2108268A1 describes the preparation of cranberry extract highly enriched in cranberry PACs of degree of polymerization greater than 5 and to use thereof to decrease the binding of certain *E. coli* bacteria to the walls of the urinary tract. The extract is obtained by a process comprising extraction with organic solvent (in particular alcohol) of the insoluble fractions obtained from cranberries. It comprises at least 15% by weight of PACs expressed in procyanidin C1 equivalents in relation to the dry weight of the extract, a quantity of anthocyans similar to that of the berry of cranberry, flavonols, and sugar residues, proteins, fibers and inorganic materials. Being obtained from insoluble cranberry fractions, it does not on the other hand include significant quantities of organic acids, such as quinic acid or phenolic acids (but only perhaps small residual quantities, largely less than 5% by weight in relation to the total weight of the dry extract).

Application WO2010/121203 describes a cranberry extract for reducing bacterial contamination in beverages, comprising PACs and anthocyans, but comprising very limited residual quantities of sugars and organic acids due to a purification step on resin binding phenolic compounds but not substantially binding sugars and organic acids. The general description indicates that the residual quantity of sugars or organic acids is in all cases less than 5%, and the examples of extracts characterized in the experimental portion all comprise less than 1% of sugars and residual organic acids.

Bactericidal and bacteriostatic effects of cranberry PACs have also been demonstrated in vitro (Sanchez-Patan et al., 2012).

EP2033641A1 describes a process for preparing PAC-rich extracts, in particular from cranberry, able to have antibacterial effects, in particular in the context of urinary tract infections. The process described and claimed involves a step of washing with demineralized water the resin used to enrich the extract in PACs, which leads to the removal of sugars and phenolic acids. Moreover, an optional step aimed at removing anthocyanidins is also described. Here again, the process described thus aims foremost to maximally enrich the extract in PACs, to the detriment of other active compounds contained in cranberry.

Thus, it has generally been considered in recent years that the positive effect of the consumption of cranberry on the prevention of urinary tract infections was related to the anti-adhesion, bacteriostatic and bactericidal effects of PACs contained in cranberry.

However, PACs have low bioavailability in their native PAC form, and only a small proportion of PACs appear to cross the intestinal barrier intact (Appeldoorn et al., 2009). Moreover, PACs appear to be less bioavailable when their degree of polymerization is high (Ou et al., 2012). Thus, most cranberry PACs remain in the intestinal lumen when passing through the small intestine to reach the colon. In this location, PACs of low polymerization are hydrolyzed in the form of phenolic acids and become bioavailable in this form.

Consequently, even if the anti-adhesion, bacteriostatic and bactericidal effects of typical cranberry PACs are proven in vitro, they cannot occur for the most part in the bladder or the urinary tract, since a very small proportion of these compounds are able to reach urinary tract. On the other hand, these effects are possible in the colon, but it is not clear if they alone can explain the positive effect of cranberry consumption on the prevention of urinary tract infections.

It is thus difficult, in view of the prior art, to determine which components of the whole berry of cranberry make it possible to avoid or decrease the occurrence of urinary tract infections.

In the context of the present invention, the inventors developed a novel cranberry extract which, instead of focusing on a particular type of component (PACs, phenolic acids, organic acids) likely to have an antibacterial effect, incorporates in a single extract fractions enriched in each of these components. Moreover, the extract according to the invention is a de-esterified extract, i.e., has been subjected, in one step or another, to enzymatic treatment with esterases, with the effect of increasing the concentration of the compounds of interest and making the extract more fermentable.

The extract according to the invention thus has the advantage of being highly concentrated in the compounds of interest in relation to the berry of cranberry, and of combining various mechanisms for preventing or reducing the occurrence of urinary tract infections.

DESCRIPTION OF THE INVENTION

The present invention thus relates to a cranberry extract, comprising:
- 5 to 20% by weight, advantageously 10 to 15% by weight, of proanthocyanidins (PACs) in relation to the total weight of the dry extract (measured by the BL-DMAC method),
- 2 to 12% by weight, advantageously 3 to 10% by weight, advantageously strictly more than 5% and less than 10% by weight, of organic acids in relation to the total weight of the dry extract, including:
  - 1-5% by weight, advantageously 1-3% by weight of quinic acid in relation to the total weight of the dry extract,
  - 0.5 to 8% by weight, advantageously 1-4% by weight, of phenolic acids in relation to the total weight of the dry extract,
- at least 0.5% by weight, advantageously at least 1% by weight, of anthocyans and/or anthocyanidins in relation to the total weight of the dry extract,
- 1-10%, advantageously 1-5% by weight, of sugars in relation to the total weight of the dry extract,
- 1-10% by weight, advantageously 2-5% by weight, of flavonols, in relation to the total weight of the dry extract.

In a preferred embodiment of the present invention, the cranberry extract is, moreover, de-esterified.

By "cranberry" is meant the plant *Vaccinium macrocarpon*, also called "American cranberry" or "large cranberry," or "atoca" or "ataca" in Quebec, or "canneberge", "canneberge d'Amérique" or "grande airelle rouge d'Amérique" in French. To simplify matters, the term "cranberry" is generally used in the present description.

By "de-esterified" is meant that the extract has undergone, during its process of preparation, a step of enzymatic treatment with at least one enzyme of the "esterase" type, able to hydrolyze certain ester bonds, selected from tannases (in particular galloyl-esterases and ellagi-esterases), cinnamoyl-esterases, ß-glucosidases and mixtures thereof. This treatment has the effect of increasing the intestinal fermentability of the extract according to the invention, by hydrolyzing, at least partially, certain complex compounds present in cranberry. Advantageously, a mixture comprising tannase, cinnamoyl-esterase and ß-glucosidase activities can be used.

By "tannase" is meant an enzyme able to hydrolyze the ester bond between the sugar and the gallic or ellagic acids of gallotannins and ellagitannins. In particular, in EC nomenclature (referring to Enzyme Commission number, a numerical classification scheme for enzymes based on the chemical reactions they catalyze) tannases have EC no. 3.1.1.20, and catalyze the following reactions:
digallate+$H_2O$=2 gallate,
ellagitannins+$H_2O$ hexahydroxydiphenic acid+gallic acid,
(+/−)-epicatechin-gallate+$H_2O$=epicatechin+gallic acid,
(+/−)-epigallocatechin-3-gallate+$H_2O$=epigallocatechin+gallic acid,
(−)-epigallocatechin gallate+$H_2O$=(−)-epigallocatechin+gallic acid,
1,2,3,4,6-pentagalloyl glucose+$H_2O$=5 gallate+D-glucose,
tannic acid+$H_2O$=10 gallate+D-glucose,
propyl gallate+$H_2O$=gallate+propanol,
protocatechuic acid ethyl ester+$H_2O$=protocatechuate+ethanol.

When tannases are used, the treatment has the effect in particular of hydrolyzing cranberry gallotannins and ellagitannins into sugars and gallic acid or ellagic acid, respectively, two phenolic acids naturally scarcely present or not present in free form in cranberry. Such enzymes are available commercially from various suppliers such as:
- AB Enzymes GmbH, Feldbergstrasse 78, 64293 Darmstadt, Germany: (Rohapect 10L; Rohament CL; Rohalase BX/BXL; Endozym B-Split)
- Biocatalysts Ltd, Cefn Coed, Parc Nantgarw, Cardiff, CF15 7QQ, Wales, U.K.: (Depol 670L, Depol 40, Depol 793L; Cellulase 13L, Tannase 795P)
- Novozymes A/S, Krogshoejvej 36, 2880 Bagsvaerd, Denmark: (Pectinex BE-3L; Pectinex Ultra SP-L)

By "ß-glucosidases" is meant an enzyme able to hydrolyze a terminal non-reducing glucose, linked to an aglycone by a B bond, with release of D-glucose. In EC nomenclature, ß-glucosidases have EC no. 3.2.1.21, and catalyze the reactions:
anthocyanidin-glucoside+$H_2O$=anthocyanidin+glucose
  with the anthocyanidin moiety: cyanidin, petunidin, malvidin, peonidin,
  and with the glucoside moiety: mainly glucose, galactose, arabinose,
quercetin-3,4'-di-beta-D-glucopyranoside+$H_2O$ quercetin+beta-D-glucose,
quercetin-4'-beta-glucopyranoside+$H_2O$ quercetin+beta-D-glucose,
quercetin-7-O-beta-D-glucoside+$H_2O$ quercetin+beta-D-glucose.

Such enzymes are available commercially from various suppliers, and in particular from those mentioned above concerning tannases.

By "cinnamoyl-esterase" is meant enzymes having EC no. 3.1.1.42 and EC no. 3.1.1.73 in EC nomenclature, and able to catalyze the following reactions:
EC. 3.1.1.42—chlorogenate hydrolase:
  chlorogenic acid+$H_2O$=caffeic acid+quinic acid,
  5-O-caffeoyl quinic acid+$H_2O$=caffeic acid+quinic acid;
EC. 3.1.1.73—feruloyl esterase:
  ferulic acid methyl ester+$H_2O$=ferulic acid+methanol,
  5-O-(trans-feruloyl)-L-arabinofuranoside+$H_2O$=ferulic acid+L-arabinose,
  5-O-p-coumaroylquinic acid+$H_2O$=p-coumaric acid+quinic acid.

Such enzymes are available commercially from various suppliers, and in particular from those mentioned above concerning tannases.

Enzymatic treatment with at least one esterase thus makes it possible also to increase the concentration of the extract, in particular in organic acids and in free phenolic acids. The enzymes described above can be used throughout the production line at variable concentrations generally from 0.05% to 0.1% of the dry matter of cranberry used.

Advantageously, enzymatic treatment with at least one enzyme of the "esterase" type, able to hydrolyze certain ester bonds, selected from tannases (in particular galloyl-esterases and ellagi-esterases), cinnamoyl-esterases, ß-glucosidases and mixtures thereof, was carried out at the same time as or following treatment with liquefaction enzymes (pectinase, polygalacturonase, cellulase) aiming mainly to:
  distinguish hydrolysable phenolic fractions from hydrolysis-resistant fractions,
  make these compounds more non-polar and consequently more easily separable.

Certain preparations comprising liquefaction enzymes (pectinase, polygalactuonase, cellulase) can in a minority have secondary activities of the cellobiase (ß-glucosidase), galactosidase, arabinosidase, xylanase type, or secondary activities of the tannase, cinnamoyl-esterase and/or ß-glucosidase type, able to lead to very limited de-esterification of cranberry polyphenols. However, the enzymatic liquefaction step does not make it possible to obtain significant de-esterification of the extract, which may be obtained only by means of an additional step of specific enzymatic treatment with at least one esterase selected from tannases (in particular galloyl-esterases and ellagi-esterases), cinnamoyl-esterases, ß-glucosidases and mixtures thereof. Consequently, cranberry extract having undergone a single enzymatic liquefaction step using a composition comprising in a large majority liquefaction enzymes of the pectinase, polygalacturonase and cellulase type, without supplemental addition of at least one esterase selected from tannases (in particular galloyl-esterases and ellagi-esterases), cinnamoyl-esterases, ß-glucosidases and mixtures thereof, will not be considered de-esterified extract in the context of the invention.

By "proanthocyanidins" or "condensed tannins" (abbreviated as "PACs") is meant oligomers or polymers of cranberry flavanols. The term "oligomer" includes flavanol dimers and trimers, and the term "polymer" includes flavanol multimers having a degree of polymerization (DP) of at least 4. De-esterified extract of cranberry according to the invention comprises both oligomers of PACs and polymers of PACs, in an overall proportion of 5 to 20% by weight, advantageously 10 to 15% by weight, of PACs in relation to the total weight of the dry extract. Within the total PACs, polymers of PACs (DP≥4) represent at least 30% by weight, in relation to the weight of all PACs present in the extract.

In vivo, polymers of PACs have low bioavailability and remain in a majority in the intestinal lumen when passing through the small intestine to reach the colon, where they are able to have an anti-adhesion, bactericidal and bacteriostatic effect on enteric bacteria capable of migrating toward the urethra and giving rise to urinary tract infections. The presence of polymers of PACs in the extract according to the invention thus contributes to its efficacy in terms of preventing or reducing urinary tract infections.

Oligomers of PACs also have low bioavailability in vivo and arrive in a majority in the colon, where they are hydrolyzed in the form of phenolic acids. These, and in particular the most non-polar such as benzoic acid, can then exert another type of bacterial effect, by disrupting possible metabolic exchanges of bacterial membrane transporters.

The extract according to the invention also comprises 2-12% by weight, advantageously 3-10% by weight, advantageously strictly more than 5% and less than 10% by weight, of organic acids in relation to the total weight of the dry extract. By "organic acid" is meant any hydrocarbon compound (saturated or unsaturated) comprising at least one acid functional group. Thus, cranberry organic acids present in the extract according to the invention include:

Phenolic acids, in a quantity of 0.5-8% by weight, advantageously 1-4% by weight, in relation to the total weight of the dry extract.
The extract according to the invention comprises in particular the main phenolic acids naturally present in cranberry: p-coumaric acid, sinapic acid, caffeic acid and ferulic acid, as well as other phenolic acids present in smaller quantities in cranberry: ortho-hydroxy-cinnamic acid, para-hydroxyphenyl acetic acid, phthalic acid and ellagic acid.
Moreover, when the extract has undergone a step of treatment with at least one esterase, the quantities of certain phenolic acids such as free gallic, ellagic, p-coumaric, ferulic and caffeic acids are increased in relation to an extract not having undergone this type of treatment.
Phenolic acids, which are able to cross the intestinal barrier, are then normally conjugated with glycine to form hippuric acid (which has a weaker bactericidal effect), before being excreted in the urine. However, due to the rather large quantities of phenolic acids present in the extract according to the invention (and in particular in a de-esterified extract having undergone enzymatic treatment with esterases), the liver's capacity to conjugate glycine may well be saturated and part of the phenolic acids, not conjugated with glycine, may reach the urine and therein exert their bactericidal effects in a preventive or curative manner. The presence in the extract of various precursors of phenolic acids (in particular quinic acid, which can be transformed into benzoic acid by reductive aromatization; oligomers of PACs, which are hydrolyzed in the form of phenolic acids in the colon; and anthocyans or anthocyanidins hydrolyzed in the form of benzoic acids in the colon) also contribute to the presence in the body of a high and sustained concentration of phenolic acids, and thus to saturation of the liver's capacity to conjugate glycine.
Other organic acids naturally present in cranberry, in particular quinic acid, citric acid and malic acid.
The extract according to the invention comprises in particular 1-5% by weight, advantageously 1-3% by weight of quinic acid in relation to the total weight of the dry extract.
Quinic acid is reduced into benzoic acid (a phenolic acid) in the colon by the enzymatic systems of intestinal flora. The benzoic acid thus obtained in the colon is not metabolized and thus can exert its bactericidal effects on bacteria present in the colon and capable of migrating in the urethra and causing urinary tract infection.
Consequently, the presence in the extract according to the invention (and in particular in a de-esterified extract having undergone enzymatic treatment with esterases) of an appreciable quantity of quinic acid contributes by a third mechanism to the ability to prevent or reduce urinary tract infections of the extract according to the invention.

The extract according to the invention also comprises at least 0.5% by weight, advantageously at least 1% by weight, of anthocyans and/or anthocyanidins in relation to the total weight of the dry extract. By "anthocyanidin" is meant a subclass of flavonoids, the base structure of which is formed of two aromatic rings A and B joined by 3 carbons forming with oxygen ring C. The six most common anthocyanidins are: cyanidin, delphinidin, pelargonidin, peonidin, petunidin and malvidin, constructed on the same flavylium skeleton responsible for the compound's color, as indicated in Table 1 below:

TABLE 1

Structure of the six most common anthocyanidins.

| Name | Structure | R³' | R⁴' | R⁵' | R³ | R⁵ | R⁶ | R⁷ |
|---|---|---|---|---|---|---|---|---|
| Cyanidin | | —OH | —OH | —H | —OH | —OH | —H | —OH |
| Delphinidin | | —OH | —OH | —OH | —OH | —OH | —H | —OH |
| Pelargonidin | | —H | —OH | —H | —OH | —OH | —H | —OH |
| Malvidin | | —OCH₃ | —OH | —OCH₃ | —OH | —OH | —H | —OH |
| Peonidin | | —OCH₃ | —OH | —H | —OH | —OH | —H | —OH |
| Petunidin | | —OCH₃ | —OH | —OH | —OH | —OH | —H | —OH |

By "anthocyans" or "anthocyanosides" or "anthocyanins" is meant glycosides of anthocyanidins, i.e., anthocyanidins bearing sugars. The saccharide moiety of anthocyanosides can be a monosaccharide (glucose, galactose, rhamnose), a disaccharide (rutinose, composed of a glucose linked to a rhamnose, xyloglucose) or at times a trisaccharide. Most anthocyanosides are 3-monosides and 3,5-diosides of anthocyanidins. 3,7-Linked diosides and 3,5,3'-linked triosides also exist. Many anthocyanosides are, moreover, acylated by:

hydroxycinnamic acids: 4-coumaric, caffeic, ferulic, sinapic acids,
benzoic acids: gallic acid,
aliphatic carboxylic acids: acetic acid, or dicarboxylic acids such as malonic, malic, oxalic, succinic acids.

These acids esterify a hydroxyl of sugar, generally on the C-6 position thereof.

When the extract has not been de-esterified, it comprises mainly anthocyans. On the other hand, when the extract has been de-esterified, it comprises mainly anthocyanidins.

Anthocyans, and more particularly anthocyanidins (present in a majority when the extract is de-esterified), have been shown also to have bactericidal activities (Pratt et al., 1960). Moreover, they also are fermented by intestinal flora, leading in the colon to their transformation into phenolic acids, and in particular into benzoic acid (Keppler et al., 2005). These compounds are thus also precursors of phenolic acids in vivo.

The extract according to the invention further comprises 1-10%, advantageously 1-5% by weight of residual sugars in relation to the total weight of the dry extract. This represents a large decrease in sugar content in relation to the berry of the cranberry shrub, in which sugars represent about 45 to 67% (Blumenthal et al., 2003) by weight of the total weight of the dry extract. The sugars present include in particular glucose, fructose, sucrose, sorbitol.

The extract according to the invention also comprises 1-10% by weight, advantageously 2-5% by weight, of flavonols, such as quercetin, in glycosylated and/or aglycone form, in relation to the total weight of the dry extract.

Thus, the extract according to the invention has a complex composition, which makes it possible to cumulate several antibacterial effects in the colon (anti-adhesion, bactericidal and bacteriostatic effects via polymers of PACs present in the colon, bactericidal effects of phenolic acids generated in the colon from oligomers of PACs and quinic acid), these synergistic effects give the extract according to the invention a strong ability to prevent or reduce the occurrence of urinary tract infections.

Moreover, the presence of phenolic acids in large quantities potentially makes possible, by means of saturation of the liver's capacity to combine phenolic acids with glycine, a direct bactericidal effect in the urinary tract, in a preventive or curative manner.

The extract according to the invention may be provided in various forms, in particular in solution form, or in dry form. Advantageously, the extract according to the invention is dry extract. In powder form, it can be used in various forms, making it possible for example to prepare tablets, capsules, granules and orodispersible solutions. In solid or liquid form it can also make it possible to formulate gel, creams, soaps for topical application, and to formulate beverages that are reconstituted by dilution or are ready to use.

The extract according to the invention may be prepared by a process according to the invention comprising the following steps:

a) Enriching a water-soluble fraction of cranberry in non-polar polyphenolic compounds (anthocyans, anthocyanidins and oligomers of PACs), on the one hand, and in organic acids, on the other hand, to obtain fraction I, b) Enriching a water-insoluble fraction of cranberry in especially-tanning polymers of PACs with mean degrees of polymerization greater than 6-7 of type B and also comprising at least one type A bond, to obtain fraction II, c) Combining fractions I (rich in non-polar polyphenolic compounds and in organic acids) and II (rich in polymers of PACs) obtained in steps a) and b), respectively, in proportions corresponding to a weight ratio (fraction I/fraction II) comprised between 20/80 and 80/20, and d) Enzymatic digestion with at least one esterase selected from tannases (in particular galloyl-esterases and ellagi-esterases), cinnamoyl-esterases, β-glucosidases and mixtures thereof.

In the process according to the invention, the extract is prepared from the combination of two fractions I and II, obtained from the water-soluble (for fraction I) and water-insoluble (for fraction II) fractions of cranberry, respectively.

These water-soluble and water-insoluble fractions of cranberry may be obtained from whole cranberries, by:

i) Crushing whole berries of cranberry,
ii) Decanting and separating the water-soluble and water-insoluble fractions.

Whole cranberries can be fresh, dried or frozen (preferably by an individually quick frozen (IQF) process). They are then crushed by standard techniques (step i)). At this stage, the crushed material is preferably subjected to a step of enzymatic liquefaction (step i1)). This step is a standard step well-known to the person skilled in the art, during which pectinases, polygalacturonases and/or cellulases are added to the crushed material in order to liquefy it. The crushed material, preferably liquefied, is then subjected to a step of decantation and separation of the water-soluble and water-insoluble fractions (step ii)). This step is advantageously carried out at a pH ranging between 2 and 7, at a temperature ranging between 15 and 70° C., and at a pressure ranging between 1 and 15 atmospheres.

Alternatively, cranberry juice, i.e., a liquid fraction of cranberry obtained by pressing berries of cranberry, can be used directly as the water-soluble fraction. The juice can, moreover, be concentrated juice. It has preferably been subjected to a step of enzymatic liquefaction with at least one pectinase, polygalacturonase, cellulase and mixtures thereof.

In the same way, cranberry marc can be used directly as the water-insoluble fraction. By "cranberry marc" or "spent cranberry" is meant the wet or dried residue of pressed berries of the cranberry shrub. These have preferably been subjected to a step of enzymatic liquefaction with at least one pectinase, polygalacturonase, cellulase and mixtures thereof.

In the process according to the invention, the water-soluble and water-insoluble fractions are treated separately: step a) for the water-soluble fraction, step b) for the water-insoluble fraction. These separate treatments can be carried out in any order: step a) then step b), step b) then step a), or simultaneous treatment in parallel of the two fractions.

In step a), the water-soluble fraction is enriched in non-polar polyphenolic compounds, on the one hand, and in organic acids, on the other hand, to obtain a fraction called "fraction I". This enrichment is carried out by two successive purification steps, followed by a combination step leading to fraction I:

In a $1^{st}$ step a1), non-polar compounds (and in particular non-polar phenolic compounds, such as flavanols, flavonols and anthocyans, optionally de-esterified) are separated from polar compounds (such as sugars and acids) by adsorption of the water-soluble fraction on a non-polar support. Washing with polar solvent makes it possible to collect the polar compounds not adsorbed on the support (the fraction called "polar fraction Ia"). A step of elution with non-polar solvent then makes it possible to collect non-polar compounds (the fraction called "non-polar fraction Ib").

The non-polar supports suitable for this separation include, for example:
  adsorption supports of the styrene/divinyl benzene copolymer type, sulfonic or non-sulfonic:
    FPX68; FPX66 (Dow Chemicals)
    Sepabeads SP411, SP70, SP700, SP852L, SP850 (Mitsubishi Chemicals);
  microporous supports supporting ionized groups of the sulfonic or tertiary amine type.
    FPA51, FPA54, FPC23H, XAD761 (Dow Chemicals),
    Diaion UBK530, UBK550, WA20, WA30.

Polar washing solvents making it possible to recover polar fraction Ia may in particular be selected from alcohols (in particular ethanol, methanol, 2-propanol).

Non-polar elution solvents making it possible to recover non-polar fraction Ib according to the selected ion-exchange resin may in particular be selected from diluted solutions of soda or potash or diluted solutions of strong hydrochloric or sulfuric acid or of weak citric acid.

At the conclusion of this step a1), non-polar fraction Ib comprising in particular non-polar phenolic compounds such as anthocyans or anthocyanidins and oligomers of PACs is set aside, whereas polar fraction Ia comprising in particular sugars and organic acids is subjected to a second purification step a2).

In a $2^{nd}$ step a2), organic acids present in polar fraction Ia are purified (and in particular separated from sugars also present in polar fraction Ia) by adsorption on ion-exchange resin (which retains organic acids, but not sugars). After washing with water (which leads in particular to removal of most sugars), a fraction called "fraction Ic" enriched in cranberry organic acids (quinic acid, citric acid, malic acid and phenolic acids in particular) is eluted using acidic aqueous solvent.

In a $3^{rd}$ step a3), fraction I, enriched in non-polar polyphenolic compounds (anthocyans, anthocyanidins and oligomers of PACs), on the one hand, and in organic acids, on the other hand, is obtained by combining fractions Ib and Ic.

In step b), the water-insoluble fraction (marc) is enriched in polymers of PACs, to obtain a fraction called "fraction II", by treatment comprising a step of extraction of polymers of PACs with organic solvent, preferably followed by steps of clarification, distillation and concentration of the enriched solution thus obtained. Various processes of this type are described in application EP2108268A1.

Thus, the organic solvent used for extraction may in particular be selected from alcohols (in particular ethanol), aldehydes (in particular acetaldehyde) and esters (in particular ethyl acetate). Advantageously, the organic solvent used is an alcohol, in particular ethanol.

The quantity of organic solvent added to the water-soluble fraction of cranberry may in particular range between 10 and 15% by volume, in relation to the volume of the water-soluble fraction of cranberry on which the extraction is carried out.

In particular, the extraction step may be carried out by hydro-alcoholic counter-current extraction, wherein hydro-alcoholic mixtures comprising from 35 to 80% of ethanol are poured successively on less and less exhausted portions of fresh cranberry marc, and wherein the ethanolic fractions comprise more and more dry matter extractable solution.

Final steps of clarification, distillation and concentration are advantageous.

Fractions I (Ib and Ic enriched in non-polar phenolic compounds such as anthocyans, anthocyanidins and oligomers of PACs, and in organic acids) and II (enriched in polymers of PACs) are then combined to form an extract enriched in these various compounds of interest. The combination may be prepared in variable proportions corresponding to a weight ratio (fraction I/fraction II) ranging between 20/80 and 80/20, advantageously between 30/70 and 70/30, 35/65 and 65/35, 40/60 and 60/40, or between 45/55 and 55/45. Advantageously, the weight ratio (fraction I/fraction II) may be close to 50/50. Indeed, this corresponds to a combination in which fractions I and II obtained at the conclusion of steps c) and d), respectively, are simply mixed, without removing part of one of the fractions. Thus, all of the compounds of interest are made use of in the extract, without loss related to exclusion of part of the compounds of interest. However, other weight ratios (fraction I/fraction II) may be used if it is desired to increase or decrease the proportion in the extract of certain compounds of interest.

The process according to the invention for preparing the extract according to the invention further comprises a step d) of enzymatic digestion with at least one esterase. This step d) aims at increasing the intestinal fermentability of the extract according to the invention, by hydrolyzing, at least partially, certain complex compounds present in cranberry, and does not interfere significantly with other steps of the preparation process. It may, consequently, be carried out at various stages of the preparation process. In particular, it may be carried out:

- before step a), during preparation of the water-soluble and water-insoluble fractions (for example between steps i) and ii), on crushed material, preferably liquefied), or on the water-soluble and water-insoluble fractions, preferably liquefied,
- between steps a) and b) and final combination step c), on fractions I and II, or
- at the end of the process, on the combined extract obtained at the conclusion of step c).

The process according to the invention may further comprise an additional step of drying the extract, in order to obtain a dry extract. Such drying may be carried out by any appropriate standard technique, and in particular by atomization, using a simple or multi-effects drying tower supplied with aqueous concentrates having dry matter greater than 20% and heated beforehand (50-80° C.). These concentrates are sprayed by systems comprising nozzles and/or turbines and are dried in powder form from droplets nebulized in a stream of dry air at temperatures below 180° C. Depending on the case, polyphenolic fractions of cranberry extracts may be dried without support in the case of non-polar extracts developed, or advantageously on supports such as carbohydrates, (maltodextrin, resistant starches, inulin). In the case of particularly acid fractions, the fractions may be neutralized by adding magnesium hydroxide before drying.

The invention also relates to an extract obtainable by the process according to the invention. Such an extract preferably comprises:

- 5 to 20% by weight, advantageously 10 to 15% by weight, of proanthocyanidins (PACs) in relation to the total weight of the dry extract,
- 2-12% by weight, advantageously 3-10% by weight, advantageously strictly more than 5% and less than 10% by weight, of organic acids in relation to the total weight of the dry extract, including:
  - 1-10% by weight, advantageously 1-5% by weight, advantageously 1-3% by weight of quinic acid in relation to the total weight of the dry extract,
  - 0.5-8% by weight, advantageously 1-4% by weight, of phenolic acids in relation to the total weight of the dry extract,
- at least 0.5% by weight, advantageously at least 1% by weight, of anthocyans in relation to the total weight of the dry extract,
- 1-10%, advantageously 1-5% by weight, of sugars in relation to the total weight of the dry extract,
- 1-10% by weight, advantageously 2-5% by weight, of flavonols, in relation to the total weight of the dry extract.

The extract obtainable by the process according to the invention may also be provided in various forms, in particular in solution form (in particular in liquid concentrate form) or in dry form. Advantageously, the extract obtainable by the process of the invention is dry extract. It may be provided in various forms, for example in powder, tablet, capsule, granules form.

The invention also relates to a food or nutraceutical composition comprising, among other things, an extract according to the invention or an extract obtainable by the process according to the invention. This composition is intended to be ingested, and thus comprises only components acceptable for this application. It may be provided in any form commonly used in foods or nutraceuticals, and in particular in the form of a powder, capsule, tablet or beverage, or in the form of topical formulas of the gels, creams or soaps type.

The extracts according to the invention comprise various cranberry compounds having antibacterial effects in vivo in the colon:

They also comprise a large quantity of phenolic acids, able to saturate the liver's capacity to combine phenolic acids with glycine, potentially making it possible for part of these phenolic acids to reach the urinary tract and to exert their bactericidal effects in a preventive or curative manner.

The extracts according to the invention are thus particularly useful for preventing and/or treating urinary tract infections.

The invention thus also relates to a pharmaceutical composition, comprising an extract according to the invention or an extract obtainable by the process according to the invention and a pharmaceutically acceptable excipient.

The invention further relates to an extract according to the invention or an extract obtainable by the process according to the invention, for use as a drug.

The invention also relates to an extract according to the invention or an extract obtainable by the process according to the invention, for use in the prevention or treatment of urinary tract infections.

The invention also relates to the use of an extract according to the invention or an extract obtainable by the process according to the invention, for the preparation of a drug, in particular a drug intended to treat or prevent urinary tract infections.

The invention further relates to a method for treating or preventing urinary tract infections in a subject (preferably human, optionally animal), comprising the (preferably oral) administration of an effective quantity of an extract according to the invention or an extract obtainable by the process according to the invention to said subject.

By "treatment" is meant the fact of reducing bacterial infection in the urinary tract. Such a reduction may be demonstrated by means of a urine analysis showing a reduction in the number of bacteria present or by a reduction of symptoms of urinary tract infection (frequent need to urinate, burning when urinating, etc.). Advantageously, the treatment eliminates the infection completely, but the term "treatment" covers any significant reduction of infection. In the context of the treatment of urinary tract infections, the extract according to the invention or the extract obtainable by the process according to the invention may be combined with another common treatment for urinary tract infections, in particular various antibiotics well-known to the person skilled in the art.

By "prevention" is meant the fact of reducing the probability of the occurrence of urinary tract infection. Advantageously, the extract according to the invention or the extract obtainable by the process according to the invention prevents any urinary tract infection during the period the extract is taken (probability of the occurrence of urinary tract infection being zero). However, the term "prevention" also covers the possibility of significantly decreasing the frequency of the occurrence of urinary tract infections in a population of patients ingesting an effective quantity of extract during the period the extract is taken, in relation to a similar population of patients not taking the extract (in which case the probability of urinary tract infection during the period the extract is taken is simply significantly decreased). For such a comparison, the populations compared must be similar, in particular concerning the proportion of subjects typically having a high frequency of occurrence of urinary tract infections.

The extract according to the invention or the extract obtainable by the process according to the invention is particularly useful for preventing or treating urinary tract infections by uropathogenic bacteria: enterobacteria, coliforms, *Escherichia coli* (more particularly so-called "mannose resistant" *E. coli* having adhesins of type I fimbriae), but also more generally Gram-positive bacteria (and in particular *Pseudomonas aeruginosa*), and other bacteria of the *Proteus mirabilis* type, species of the genus *Staphylococcus* (in particular *Staphylococcus aureus*), species of the genus *Saprophyticus*, and species of the genus *Klebsiella*. In an embodiment, the extract according to the invention or the extract obtainable by the process according to the invention may be used to prevent or treat urinary tract infections by *Escherichia coli*. In another embodiment, the extract according to the invention or the extract obtainable by the process according to the invention may be used to prevent or treat urinary tract infections by *Pseudomonas aeruginosa*.

In still another embodiment, the extract according to the invention or the extract obtainable by the process according to the invention may be used to prevent or treat urinary tract infections by fungi, and in particular by species of the genus *Candida*, particularly *Candida albicans*.

The extract according to the invention or the extract obtainable by the process according to the invention is particularly useful in preventing the recurrence of urinary tract infections, in patients suffering from more or less frequent recurring urinary tract infections.

The extract according to the invention or the extract obtainable by the process according to the invention may be administered in particular to patients recovering from urinary tract infection, in order to decrease the probability of recurrence. The extract is thus administered in effective quantities for several days (3, 4, 5, 6 or 7 days, for example) to several weeks (2, 3, 4, 5 or 6 weeks, for example).

By "effective quantity" is meant a quantity making it possible to obtain a treatment or preventive effect (as defined above) in the subject of interest. An effective quantity of dry extract according to the invention may in particular range between 100 and 1000 mg/kg/day, advantageously between 150 and 450 mg/kg/day.

DESCRIPTION OF THE FIGURES

FIG. 4. Bactericidal effects of various extracts on *Pseudomonas aeruginosa* (ATCC 9027): (A) Growth of *Pseudomonas aeruginosa* bacteria (ATCC 9027) in culture medium lacking extract (Control without extract), in the presence of fraction Ib at 0.5 g/l, fraction (Ic+II) at 0.5 g/l, or the mixture of fraction Ib and fraction (Ic+II) at 0.5 g/l total (i.e., 0.25 g/l of fraction Ib and 0.25 g/l of fraction (Ic+II), Combined extract), for a count without filtration. The results corresponding to the mean of the results obtained with each of fractions Ib, on the one hand, and (Ic+II), on the other hand, are also indicated. (B) Growth of *Pseudomonas aeruginosa* bacteria (ATCC 9027) in culture medium lacking extract (Control without extract), in the presence of fraction Ib at 0.1 g/l, fraction (Ic+II) at 0.1 g/l, or the mixture of fraction Ib and fraction (Ic+II) at 0.1 g/l total (i.e., 0.05 g/l of fraction Ib and 0.05 g/l of fraction (Ic+II), Combined extract), for a count after filtration of aggregates. The results corresponding to the mean of the results obtained with each of fractions Ib, on the one hand, and (Ic+II), on the other hand, are also indicated.

EXAMPLES

Example 1. Preparation of De-Esterified Extract of Cranberry According to the Invention Five kilograms of IQF cranberry was crushed using a hammer mill and the 400 g of dry matter of the crushed material thus obtained was diluted by 2. The mass of crushed material was divided in half and either treated directly or subjected to enzymatic treatment in water arising from a mixture of enzymes comprising:

0.05 g of Pectinex Ultra-SP L,
0.05 g of tannase 795P,
0.05 g of cellulase 13L, and
0.05 g of Endozym B-Split.

The mixture was carried at 40° C. for 4 hours, with mixing.

The two portions of ground material were then pressed and the two juices obtained were clarified by centrifugation (3000 rpm, 10 min) and the supernatants were refrigerated. The centrifugation pellets were added to two cranberry marcs obtained in parallel.

The marcs were then extracted with a hydroalcoholic mixture of 75% ethanol v/v for a ratio of 3 to 1, the hydroethanolic solution thus obtained was filtered on a PTFE filter, 0.2 µm pore size, then concentrated under vacuum at moderate temperature (50° C.) in order to obtain a concentrated suspension which was dried by lyophilization.

The juice fractions obtained were passed through an adsorption column filled with 200 ml of Sepabeads SP411 resin (BV), at the rate of 600 ml/h; the remaining juice is then washed with 800 ml of water and the column is finally eluted with 400 ml of ethanol. The eluate obtained is finally concentrated by evaporation under vacuum (50° C.) and taken up in water and lyophilized to form fractions Ia having undergone or not having undergone enzymatic hydrolysis.

The partially bleached aqueous extracts (Fraction Ib) were then passed on an anion-exchange resin filled with 200 ml of FPA51 resin, converted beforehand to its chloride form with 400 ml of 0.1% hydrochloric acid, and rinsed with water. Fractions Ib were passed on the resin at a rate of 600 ml/h and were washed with 400 ml of water. The organic acids retained were eluted with 400 ml of 0.05% hydrochloric acid, then concentrated under vacuum forming fraction Ic.

Example 2. Characterization of the Extract According to the Invention

The extract produced in Example 1 was characterized.

The chromatographic profiles using reversed-phase UPLC at 280 nm of fractions Ib and II obtained with or without preliminary enzyme treatment (Pectinex Ultra SP-L; Cellulase 13L; Tannase 795P; B-split) at 0.05% of dry matter employed in the crushed cranberry material are presented in FIGS. 1 and 2, respectively.

Figure 1:
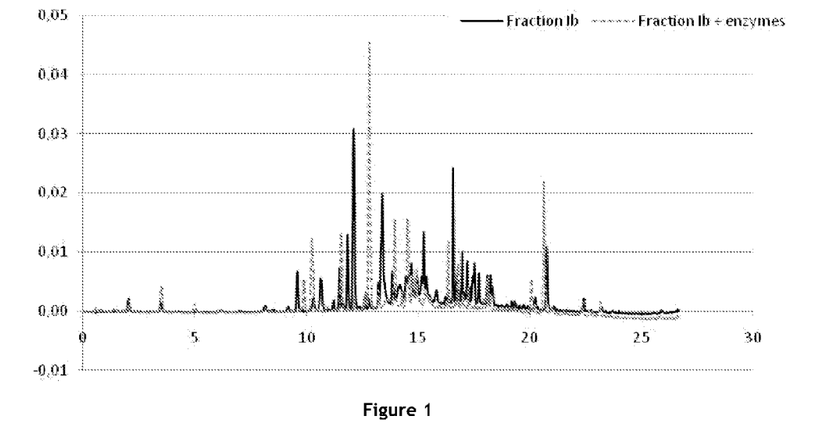
FIG. 1: Chromatographic profiles using reversed-phase UPLC at 280 nm of fractions Ib obtained with or without preliminary enzyme treatment (Pectinex Ultra SP-L; Cellulase 13L; Tannase 795P; Endozym B-split) at a concentration of 0.05% of dry matter employed in the crushed cranberry material.
Figure 2:
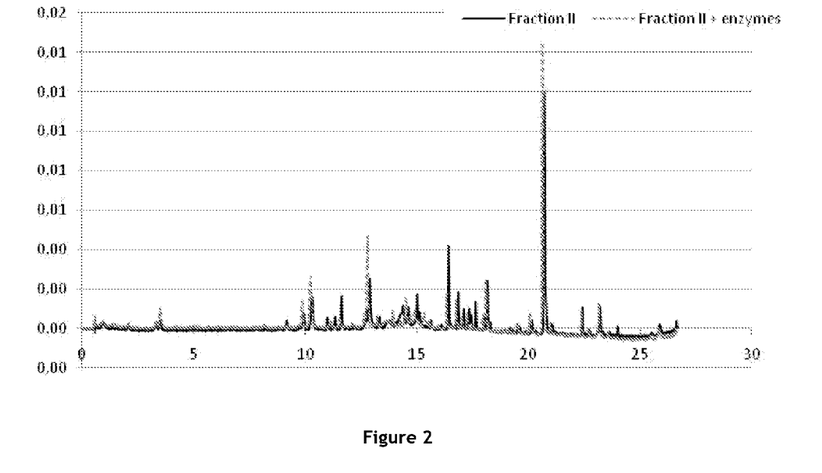
FIG. 2: Chromatographic profiles using reversed-phase UPLC at 280 nm of fractions II obtained with or without preliminary enzyme treatment (Pectinex Ultra SP-L; Cellulase 13L; Tannase 795P; B-split) at a concentration of 0.05% of dry matter employed in the crushed cranberry material.

These figures clearly show the effect of de-esterification (treatment with at least one esterase) on modification of the composition of the extract.

The analyses of the various fractions of interest obtained are described in Table 2 below. The phenolic fractions Ib and II may advantageously be supplemented with the organic acids of eluate Ic.

TABLE 2

Characterization of de-esterified fractions obtained using esterases during extraction

| In g/100 g | | Fraction Ib | Fraction Ic | Fraction II |
|---|---|---|---|---|
| Organic acids | | | | |
| Malic acid | | 0.11% | 11.88% | 1.93% |
| Quinic acid | | 0.25% | 33.26% | 3.17% |
| Citric acid | | 0.18% | 14.21% | 3.12% |
| Phenolic acids | | | | |
| Gallic acid | | 0.07% | 0.59% | 0.33% |
| Protocatechuic acid | | 0.06% | 0.43% | 0.05% |
| Benzoic acid | | 0.37% | 1.48% | 0.48% |
| Cinnamic acids | | | | |
| p-Coumaric acid | | 0.31% | 2.48% | 1.40% |
| Caffeic acid | | 0.07% | 0.49% | 0.06% |
| Ferulic acid | | 0.05% | 0.20% | 0.07% |
| Anthocyans | Cyanidol eq. | 1.03% | nd | 0.25% |
| Flavonols | Quercetin eq. | 3.24% | nd | 1.70% |
| Proanthocyanidins | | | | |
| | DMAC | 16.10% | nd | 5.70% |
| | European Pharmacopoeia | 88.6% | nd | 35.50% |

Among the fractions obtained, fractions Ib and II may be combined with liquid concentrate Ic containing the essential organic acids of cranberry, thus making it possible to formulate specific dry extracts containing both polyphenols and polar acids.

Example 3. Formulations Comprising the Extract According to the Invention

Various types of tablets containing the extracts developed can be envisaged, the general goal of this approach being to increase both the bactericidal and the bacteriostatic potential of the various active components of cranberry directly in the form of phenolic acids and procyanidols agglomerated in the colon or in the form of phenolic acids once absorbed in the general circulation and excreted in the urine.

It is important here to recall that in the colon, preservation of the tanning ability of type B and A proanthocyanidins implies that the ortho-diphenolic functional groups they comprise have not been oxidized beforehand and/or mobilized by proteins and amino acids of the food bolus.

Typically, to limit these interactions during digestion several solutions may be envisaged:
  limiting protein intake during treatment and when taking cranberry active agents may thus promote the efficacy of the cranberry extracts developed.
  favoring enteric extended-release dosage forms.
  supplementing the formula of the dietary supplement with a reducing agent able to slow oxidation of polyphenols; typically ascorbic acid can play this role. Moreover, its reducing power can contribute directly or indirectly to reduction in the colon of quinic acid into benzoic acid.

The compositions of traditional tablets may be developed favoring enteric extended release in order to limit interactions. Consequently, the galenic compositions selected will be important in order to target uropathogenic flora sensitive to the effect of phenolic compounds of cranberry, at the same time:
  Phenolic acids directly present in the extract employed,
  Quinic acid precursor of benzoic acid produced by reduction by intestinal flora,
  Flavonols and anthocyans, as well as flavanol monomers and proanthocyanidin oligomers comprising type B and type A bonds fermentable by intestinal flora, precursors of phenolic acids.

The bacteriostatic, agglomerating effect of poorly fermentable cranberry proanthocyanidin tannin polymers, i.e., higher molecular weight proanthocyanidins preferentially comprising several type A bonds.

The tablet is swallowed, and then it dissolves and must thus be absorbed throughout the gastrointestinal tract. A large variety of supports may be used, including lactose, calcium phosphate, starch, microcrystalline cellulose, modified celluloses such as, for example, hydroxypropyl methylcellulose and hydroxyethylcellulose. Formulas with coating agents such as sugar, varnish or wax to mask taste may also be envisaged in order to increase the tablet's resistance when passing through the stomach. These coatings make the tablets resistant to stomach acids so that they disintegrate in the duodenum, jejunum and colon as a result of the action of enzymes and/or alkaline pH.

Target tablets using the cranberry extracts developed comprise a tablet preparation which generally contains:
- 5 to 25% of cranberry extract (active substance);
- 0 to 10% of reducing agent, typically ascorbic acid.
- 70 to 85% of matrix loads allowing cohesion and compression, typically cellulose-based polymers,
- 0 to 15% of compounds which ensure the easy disintegration, disaggregation and dissolution of the tablet in the stomach or intestine.
- 0 to 10% of lubricating agents, glidants, waxes and coating agents, and additional binders.

Disintegration time may be modified to obtain a fast effect or for extended release.

As described below, the various fractions, in synergy with the enteric release pharmacokinetics of the tablets, make it possible to control the use of all of the active agents of cranberry.

As described in Table 3 above, the extraction methods and the various sources of cranberry polyphenols (fruit, juice, marc) mentioned above make it possible to differentiate several compositions comprising the bacteriostatic and bactericidal activities of interest in the context of:

treatment of the fast-cure type, more particularly bactericidal, synergistic bacteriostatic and bactericidal treatment, "anti-recurrence" or "preventive" treatment, primarily bacteriostatic.

It is known that the risk of the appearance of urinary tract infections is increased by low water intake. Promoting greater water consumption in the context of treatment (at least 2 liters per day) with extracts of the invention makes it possible to formulate orodispersible solutions or diluted beverages particularly well suited to the treatment envisaged. The simple extracts and/or synergistic mixtures thereof described above are first mixed with fibers, i.e., colloids resistant to upper digestive hydrolysis (stomach acid pH, enzymes of the small intestine), thus promoting the release of cranberry tannins in the colon.

TABLE 4

Composition example of diluted beverage and so-called "instant beverage" reconstituted form thereof

| Composition of instant beverage | % in g/ 100 g | Diluted beverage to be reconstituted in g/l |
|---|---|---|
| Cranberry extract | 1.6% | 0.25 |
| Pre-gelled resistant starch | 15.6% | 2.5 |
| Maltodextrin | 6.2% | 1 |
| Xanthan gum | 0.9% | 0.15 |
| Citric acid | 12.5% | 2 |
| Sucrose | 62.3% | 10 |

TABLE 3

Composition examples of 500 mg enteric extended-release tablets specially formulated in the context of curative treatment, complete synergistic treatment or preventative treatment, and allowing permanent metabolic transfer of the active agents of cranberry.

| In the context of a 15-day treatment (2 × 500 mg/day) Dissolution rate | | Curative treatment Fast dissolution Metabolizable precursors | | Complete synergistic treatment Moderate dissolution Metabolizable precursors and tannins | | Preventive treatment Slow dissolution Essentially poorly metabolized tannins | |
|---|---|---|---|---|---|---|---|
| Mixture | Type | mg | % | mg | % | mg | % |
| Cranberry extract | Fraction I | 100 | 20% | 60 | 12% | 20 | 4% |
| Cranberry extract | Fraction II | 20 | 4% | 60 | 12% | 100 | 20% |
| Ascorbic acid | | 40 | 8% | 40 | 8% | 40 | 8% |
| Hydroxypropyl-methylcellulose | Metoloses 90SH 4000SR | 50 | 10% | 70 | 14% | 90 | 18% |
| Diluent | Microcel | 217.5 | 44% | 217.5 | 44% | 217.5 | 44% |
| | Lactose | 55 | 11% | 35 | 7% | 15 | 3% |
| Talc | | 10 | 2% | 10 | 2% | 10 | 2% |
| Colloidal silica | Aerosil | 2.5 | 0.50% | 2.5 | 0.50% | 2.5 | 0.50% |
| Mg stearate | | 5 | 1% | 5 | 1% | 5 | 1% |
| Total | | 500 | 100% | 500 | 100% | 500 | 100% |

TABLE 4-continued

Composition example of diluted beverage and so-called "instant beverage" reconstituted form thereof

| Composition of instant beverage | % in g/ 100 g | Diluted beverage to be reconstituted in g/l |
|---|---|---|
| Acesulfame K; sucralose | 0.05% | 0.01 |
| Sodium chloride | 0.6% | 0.1 |
| Total | 100.0% | 16.05 |

Example 4. Antimicrobial Effects of the Extract According to the Invention

The antimicrobial effects of the extract according to the invention were tested and compared with those of simpler extracts, comprising:

Fraction Ib as obtained in Example 1 and characterized in Example 2: fraction comprising mainly proanthocyanidins (PACs) of mean degree of polymerization of about 4, as well as anthocyans. This fraction contains only very few organic acids (see Table 2 above). The antibacterial effect of this fraction may be related to PACs and/or anthocyans.

Fractions Ic and II (Ic+II) as obtained in Example 1 and characterized in Example 2: mixture comprising a small proportion of PACs of mean degree of polymerization of about 8, as well as a high proportion of organic acids (see Table 2 above). The antibacterial effect of this mixture is mainly related to organic acids present (and in particular to the most non-polar phenolic acids), and possibly partially to PACs.

In particular, the ability of fractions Ib, (Ic+II), a 50/50 mixture of fractions Ib and (Ic+II) by weight, to inhibit the proliferation of various microorganisms was measured in order to demonstrate possible synergy between the two types of extracts, one being rather centered on organic acids, the other rather on PACs and anthocyans.

Five microorganisms were selected:

Three species of bacteria known to be involved in urinary tract infections:

*Escherichia coli* (ATCC 8739): this Gram-negative bacterium is responsible for a significant proportion of urinary tract infections (Orenstein et al., 1999, Shigemura et al., 2005) and it is thus essential for the extract according to the invention to have an inhibitory action on this bacterium.

*Pseudomonas aeruginosa* (ATCC 9027): this Gram-negative bacterium is responsible for a more or less significant proportion (according to the origin of the infection and the geographic origin of the patient) of urinary tract infections (Orenstein et al., 1999, Shigemura et al., 2005), in particular complicated infections. Indeed, it often leads to persistent, chronic, antibiotic-resistant and finally recurring infections. It thus would also be useful for the extract according to the invention to have an inhibitory action on this bacterium.

*Staphylococcus aureus* (ATCC 6538): this Gram-positive bacterium is also found in certain urinary tract infections (Shigemura et al., 2005). Moreover, certain strains are resistant to traditional antibiotics and thus it would also be useful for the extract according to the invention to have an inhibitory action on this bacterium.

Two fungus strains:

*Candida albicans* (ATCC 10231): this fungus is responsible for a certain number of urinary tract infections, in particular in patients at risk because of their advanced age, chronic diseases such as diabetes, or extended immunosuppressant or anti-cancer treatments (Krcmery et al., 1999).

*Aspergillus brasiliensis* (ATCC 16404): this fungus is not particularly known to be associated with urinary tract infections, but constitutes a study model for quantifying effects on molds.

The selected strains correspond in addition to strains recommended in current regulatory methods for testing preservation efficacy and contamination of foods or hygiene products.

The microorganisms were inoculated in suitable culture medium and grown in 96-well plates. A count of microorganisms was carried out at days 1, 3, 7, 14 and 21 using a triphenyltetrazolium (TTC) assay for the three bacterial strains and *Candida albicans*. This test rests on the transformation of white TTC into red triphenylformazan (TPF) by living, multiplying cells. The detection of TPF then makes it possible to estimate the number of microorganisms present in the medium. For *Aspergillus brasiliensis*, a standard dish count is carried out.

The microorganisms are counted either directly on the culture, or after filtering the culture to eliminate aggregates. Indeed, PACs are known to aggregate bacteria by forming piles in culture, thus limiting the formation of biofilms or interaction of the bacteria with infected mucous membranes. Identifying the presence of such aggregates is thus important, and the results obtained after filtration are most representative of the overall effects of the extracts tested.

The results obtained are presented in FIGS. 3 to 6 for four of the microorganisms tested.

*Escherichia coli*

Figure 3:
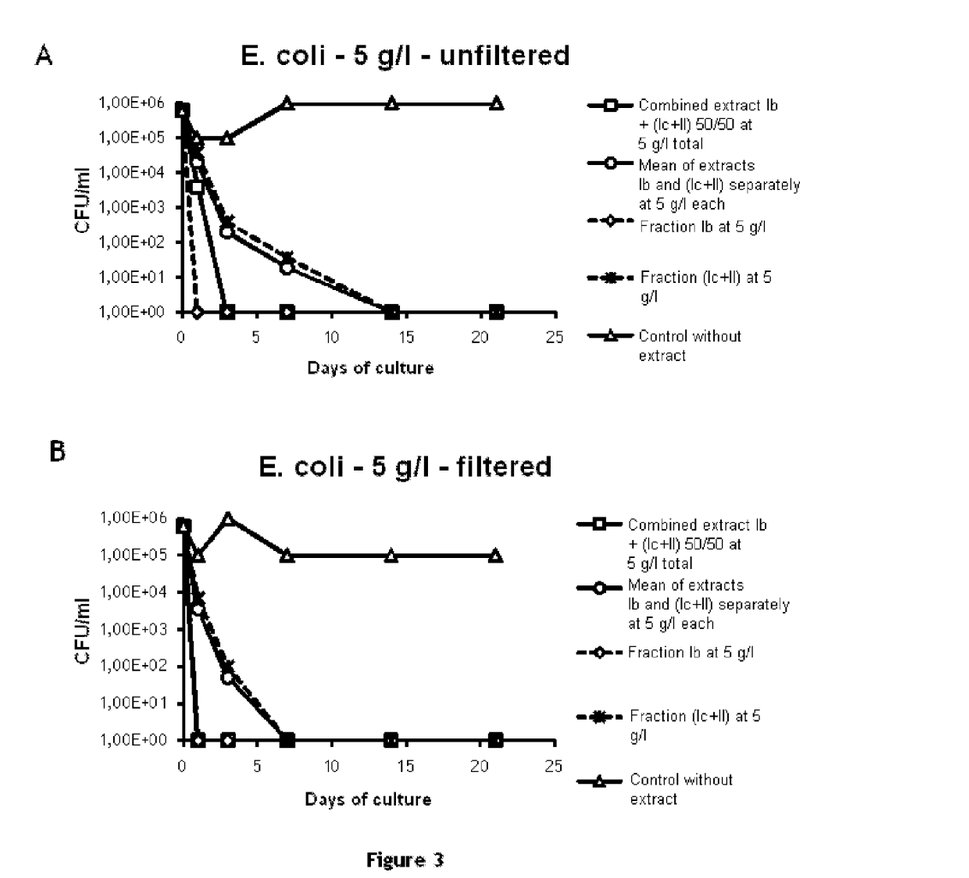
FIG. 3. Bactericidal effects of various extracts on *Escherichia coli* (ATCC 8739): growth of *Escherichia coli* bacteria (ATCC 8739) in culture medium lacking extract (Control without extract), in the presence of fraction Ib at 5 g/l, fraction (Ic+II) at 5 g/l, or the mixture of fraction Ib and fraction (Ic+II) at 5 g/l total (i.e., 2.5 g/l of fraction Ib and 2.5 g/l of fraction (Ic+II), Combined extract), for a count without filtration (A) or after filtration of aggregates (B). The results corresponding to the mean of the results obtained with each of fractions Ib, on the one hand, and (Ic+II), on the other hand, are also indicated.

FIGS. 3A and 3B, respectively, show growth of the bacteria in culture medium lacking extract, in the presence of fraction Ib at 5 g/l, fraction (Ic+II) at 5 g/l, or the mixture of fraction Ib and fraction (Ic+II) at 5 g/l total (i.e., 2.5 g/l of fraction Ib and 2.5 g/l of fraction (Ic+II)). The results corresponding to the mean of the results obtained with each of fractions Ib, on the one hand, and (Ic+II), on the other hand, are also indicated. The results are presented for measurements without filtration (FIG. 3A) or with filtration of aggregates (FIG. 3B).

In the absence of filtration, fraction Ib is more effective than fraction (Ic+II) in inhibiting *E. coli* growth in vitro. The combined extract (mixture of fractions Ib and (Ic+II)) is almost as effective as fraction Ib alone, even though it contains only half the concentration of fraction Ib in relation to fraction Ib alone. Moreover, the results obtained with the combined extract are much better than the mean of the results obtained with each of fractions Ib and (Ic+II) separately. These results suggest a synergistic effect.

When counting is carried out after filtration of aggregates, fraction Ib is even more effective than fraction (Ic+II) in inhibiting *E. coli* growth in vitro. The combined extract (mixture of fractions Ib and (Ic+II)) is as effective as fraction Ib alone, even though it contains only half the concentration of fraction Ib in relation to fraction Ib alone. Moreover, the results obtained with the combined extract are much better than the mean of the results obtained with each of fractions Ib and (Ic+II) separately. Here again, these results suggest a synergistic effect between the two fractions tested (Ib/Ic+II).

*Pseudomonas aeruginosa*

Figure 4:
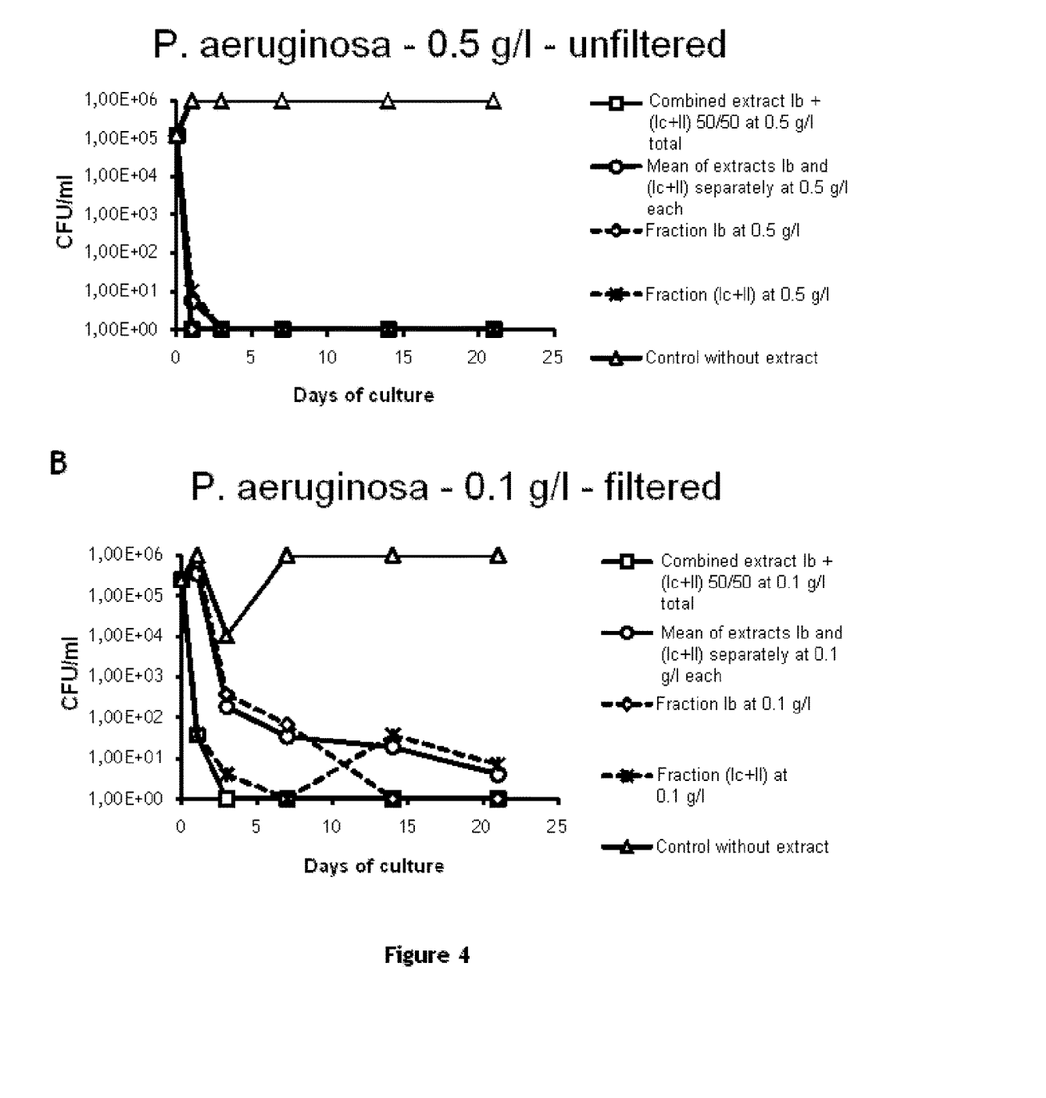

FIG. 4A shows the growth of bacteria in culture medium lacking extract, in the presence of fraction Ib at 0.5 g/l, fraction (Ic+II) at 0.5 g/l, or the mixture of fraction Ib and fraction (Ic+II) at 0.5 g/l total (i.e., 0.25 g/l of fraction Ib and 0.25 g/l of fraction (Ic+II)), with counting carried out without filtration of aggregates likely to be present in the culture.

Fraction Ib is slightly more effective than fraction (Ic+II) in inhibiting *Pseudomonas aeruginosa* growth in vitro. The combined extract (mixture of fractions Ib and (Ic+II)) is as effective as fraction Ib alone, even though it contains only half the concentration of fraction Ib in relation to fraction Ib alone. Moreover, the results obtained with the combined extract are better than the mean of the results obtained with each of fractions Ib and (Ic+II) separately. These results suggest a synergistic effect.

FIG. 4B shows the growth of bacteria in culture medium lacking extract, in the presence of fraction Ib at 0.1 g/l, fraction (Ic+II) at 0.1 g/l, or the mixture of fraction Ib and fraction (Ic+II) at 0.1 g/l total (i.e., 0.05 g/l of fraction Ib and 0.05 g/l of fraction (Ic+II)), with counting carried out after filtration of aggregates likely to be present in the culture.

This time, fraction (Ic+II) is more effective than fraction Ib in inhibiting *Pseudomonas aeruginosa* growth in vitro. The combined extract (mixture of fractions Ib and (Ic+II)) is more effective than each fraction Ib or (Ic+II) alone, even though it contains only half the concentration of fraction Ib in relation to fraction Ib alone, since it acts more quickly than each fraction Ib or (Ic+II) alone. These results clearly show the existence of a synergistic effect between the two fractions tested (Ib/Ic+II).

*Staphylococcus aureus*

Figure 5:
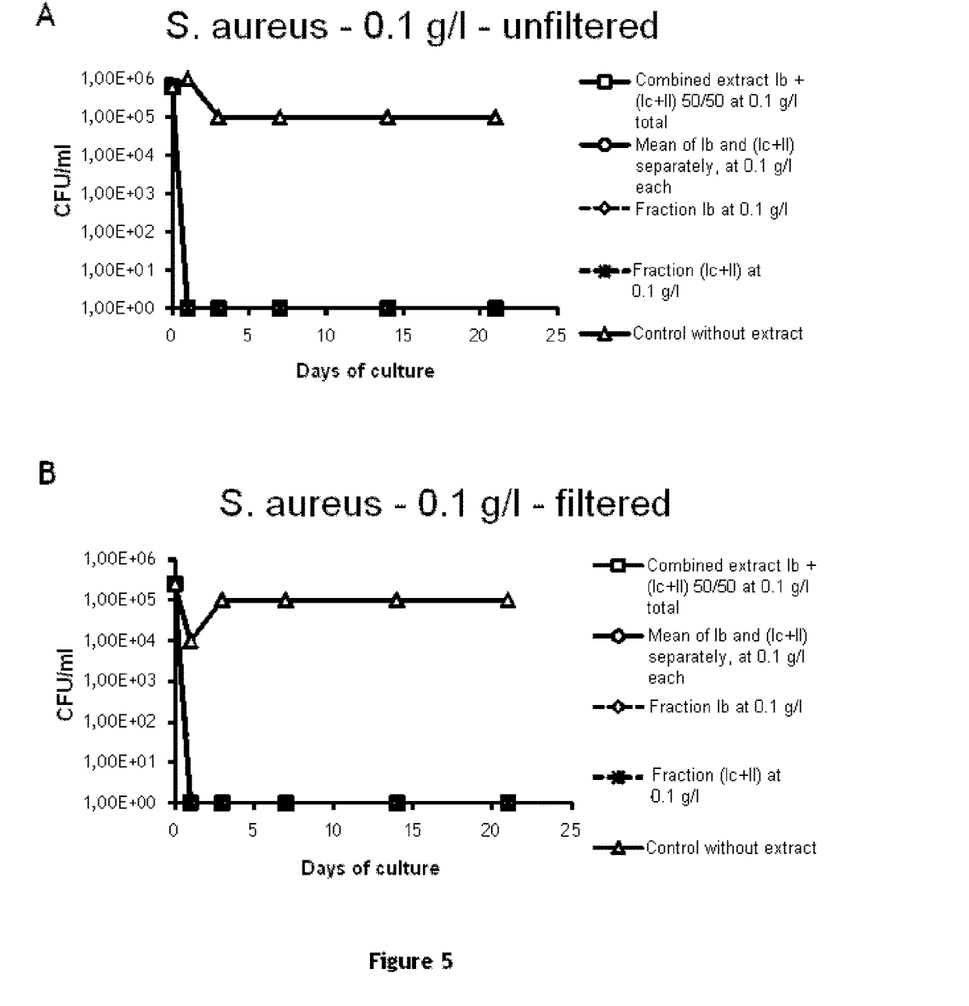
FIG. 5. Bactericidal effects of various extracts on *Staphylococcus aureus* (ATCC 6538): growth of *Staphylococcus aureus* bacteria (ATCC 6538) in culture medium lacking extract (Control without extract), in the presence of fraction Ib at 0.1 g/l, fraction (Ic+II) at 0.1 g/l, or the mixture of fraction Ib and fraction (Ic+II) at 0.1 g/l total (i.e., 0.05 g/l of fraction Ib and 0.05 g/l of fraction (Ic+II), Combined extract), for a count without filtration (A) or after filtration of aggregates (B). The results corresponding to the mean of the results obtained with each of fractions Ib, on the one hand, and (Ic+II), on the other hand, are also indicated.

FIGS. 5A and 5B, respectively, show the growth of bacteria in culture medium lacking extract, in the presence of fraction Ib at 5 g/l, fraction (Ic+II) at 5 g/l, or the mixture of fraction Ib and fraction (Ic+II) at 5 g/l total (i.e., 2.5 g/l of fraction Ib and 2.5 g/l of fraction (Ic+II)). The results corresponding to the mean of the results obtained with each of fractions Ib, on the one hand, and (Ic+II), on the other hand, are also indicated. The results are presented for measurements without filtration (FIG. 5A) or with filtration of aggregates (FIG. 5B).

In both cases, each of the extracts separately and the combined extracts are extremely effective in inhibiting *Staphylococcus aureus* growth in vitro, to the extent that the conditions tested do not make it possible to demonstrate synergy between the two extracts, each of the extracts being maximally effective already. The presence of synergy cannot, however, be excluded, and could perhaps be shown by using lower concentrations of the extracts. The effects of the combinations of phenolic fractions are clearly strain-dependent, and the cell wall of *Staphylococcus aureus*, a Gram-positive strain, is particularly sensitive to the effects of the fractions tested here.

*Candida albicans*

Figure 6:
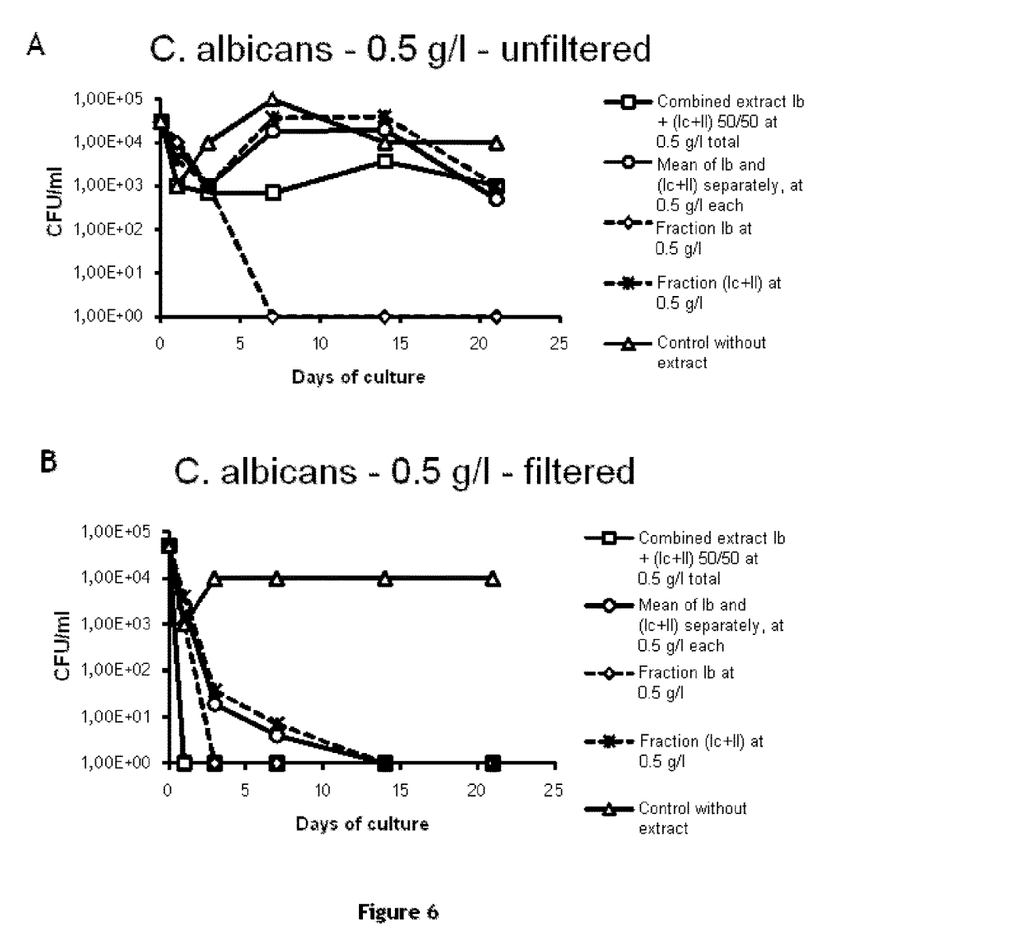
FIG. 6. Fungicidal effects of various extracts on *Candida albicans* (ATCC 10231): growth of *Candida albicans* fungi (ATCC 10231) in culture medium lacking extract (Control without extract), in the presence of fraction Ib at 0.5 g/l, fraction (Ic+II) at 0.5 g/l, or the mixture of fraction Ib and fraction (Ic+II) at 0.5 g/l total (i.e., 0.25 g/l of fraction Ib and 0.25 g/l of fraction (Ic+II), Combined extract), for a count without filtration (A) or after filtration of aggregates (B). The results corresponding to the mean of the results obtained with each of fractions Ib, on the one hand, and (Ic+II), on the other hand, are also indicated.

FIGS. 6A and 6B, respectively, show the growth of fungi in culture medium lacking extract, in the presence of fraction Ib at 0.5 g/l, fraction (Ic+II) at 0.5 g/l, or the mixture of fraction Ib and fraction (Ic+II) at 0.5 g/l total (i.e., 0.25 g/l of fraction Ib and 0.25 g/l of fraction (Ic+II)). The results corresponding to the mean of the results obtained with each of fractions Ib, on the one hand, and (Ic+II), on the other hand, are also indicated. The results are presented for measurements without filtration (FIG. 6A) or with filtration of aggregates (FIG. 6B).

In the absence of filtration, fraction Ib is clearly more effective than fraction (Ic+II) in inhibiting *Candida albicans* growth in vitro. The combined extract (mixture of fractions Ib and (Ic+II)) has an intermediate inhibitory activity, however one better than the mean of the results obtained with each of fractions Ib and (Ic+II) separately.

When counting is carried out after filtration of aggregates, fraction Ib is even more effective than fraction (Ic+II) in inhibiting *Candida albicans* growth in vitro. The combined extract (mixture of fractions Ib and (Ic+II)) is more effective than each fraction Ib or (Ic+II) alone, even though it contains only half the concentration of fraction Ib in relation to fraction Ib alone, since it acts more quickly than each fraction Ib or (Ic+II) alone. These results clearly show the existence of a synergistic effect between the two fractions tested (Ib/Ic+II).

*Aspergillus brasiliensis*

No significant inhibition for any of the extracts tested was observed.

CONCLUSION

The results presented above clearly show that the extract according to the invention, which combines fractions Ib, Ic and II, has antimicrobial activity on three bacteria and one fungus known to be responsible for urinary tract infections.

Moreover, at least under certain conditions, a synergistic effect between fraction Ib, rich in PACs of mean degree of polymerization of about 4 and also comprising anthocyans, on the one hand, and fraction Ic+II, rich in organic acids and also comprising a proportion of PACs of mean degree of polymerization of about 8, on the other hand, could be shown, thus demonstrating the great advantage of the extract according to the invention, which combines the various active products of cranberry in concentrated form, to improve the treatment or prevention of urinary tract infections.

It should be noted that the synergy between the various active components of the extract according to the invention may be even more marked in vivo.

Indeed, in vivo, the effect of organic acids, and in particular the most non-polar phenolic acids such as benzoic acid, is potentially limited in the urine due to their conjugation with glycine to form hippuric acid when they are in enterohepatic circulation, before being excreted in the urine.

However, the extract according to the invention comprises, in addition to phenolic acids, various precursors of these acids, and in particular of benzoic acid. This is the case with quinic acid, which can be transformed into benzoic acid by reductive aromatization. It is also the case of oligomers of PACs, which do not cross the intestinal barrier, but are fermented by intestinal flora and cleaved to form short-chain phenolic acids. Thus, in addition to their effect of aggregating microorganisms in the digestive tract, PACs are also of use as precursors of phenolic acids. Moreover, the degree of polymerization of PACS has a strong influence on their fermentability by intestinal flora, as has been shown for type B PACs of apple (Bazzocco et al., 2008). PAC oligomers are more prone to produce phenolic acids, whereas higher, less fermentable polymers can inhibit the flora by aggregation. This effect is also responsible for reduction of populations of flora in experiments after filtration compared with reduction without filtration. In the case of *Pseudomonas aeruginosa* without filtration at 0.5 g/l, the effect of fraction (Ic+II) alone is less than that of fraction Ib alone (FIG. 4A). In comparison, the effect for the same fractions at 0.1 g/l after filtration is reversed. After filtration, fraction (Ic+II) alone is more effective, whereas it comprises less PAC than fraction Ib but is more polymerized, thus effectively forming aggregates. These effects are particularly suited to the formulation of a curative treatment, an initial treatment or an anti-recurrence treatment by modifying the proportions of the various fractions as described in Table 3.

Finally, this is also the case for anthocyans and/or anthocyanidins, which are, like oligomers of PACs, fermented by intestinal flora and cleaved to form short-chain phenolic acids in the colon, including benzoic acids.

The combination in the extract according to the invention of the presence of phenolic acids and various precursors leading more or less quickly to new phenolic acids has the advantage of resulting in higher concentration of phenolic acids, sustained over time, thus making it potentially possible to saturate the phenolic acid conjugation system with glycine to form hippuric acid, non-conjugated phenolic acids, which are more active and thus able to reach the urine, which has little chance to occur when phenolic acids alone are present.

BIBLIOGRAPHICAL REFERENCES

Appeldoorn, M. M., Vincken, J. P., Gruppen, H., and Hollman, P. C. (2009) Procyanidin dimers A1, A2, and B2 are absorbed without conjugation or methylation from the small intestine of rats, J Nutr 139, 1469-1473;

Blumenthal M, Hall T, Goldberg A, Kunz T, Kinda K, editors. 2003. The ABC Clinical Guide to Herbs. Austin (Tex.): American Botanical Council.

Cong, D., Fong, A. K., Lee, R., and Pang, K. S. (2001) Absorption of benzoic acid in segmental regions of the vascularly perfused rat small intestine preparation, Drug Metab Dispos 29, 1539-1547;

EP0752871B1;
EP1014969B1;
EP2033641A1;
EP2108268A1;

Bazzocco, S.; Mattila, I., Guyot, S.; Renard, C. M. G. C.; Aura, A-M. Factors affecting the conversion of apple polyphenols to phenolic acids and fruit matrix to short-chain fatty acids by human faecal microbiota in vitro. *European Daynal of Nutrition* vol. 47 issue 8 Dec. 2008. p. 442-452.

Gu, L., Kelm, M., Hammerstone, J. F., Beecher, G., Cunningham, D., Vannozzi, S., and Prior, R. L. (2002) Fractionation of polymeric procyanidins from lowbush blueberry and quantification of procyanidins in selected foods with an optimized normal-phase HPLC-MS fluorescent detection process, J Agric Food Chem 50, 4852-4860;

Keppler K, Humpf H U. Metabolism of anthocyanins and their phenolic degradation products by the intestinal microflora. Bioorg Med Chem. 2005 Sep. 1; 13(17):5195-205.

Krcmery S, Dubrava M, Krcmery V Jr. Fungal urinary tract infections in patients at risk. Int J Antimicrob Agents. 1999 May; 11(3-4):289-91.

Orenstein R, Wong E S. Urinary tract infections in adults. Am Fam Physician. 1999 Mar. 1; 59(5):1225-34, 1237.

Ou, K., Percival, S. S., Zou, T., Khoo, C., and Gu, L. (2012) Transport of cranberry A-type procyanidin dimers, trimers, and tetramers across monolayers of human intestinal epithelial Caco-2 cells, J Agric Food Chem 60, 1390-1396;

Pratt, D. E., Powers, J. J. and Somaatmadja, D. (1960) Anthocyanins. I. The influence of strawberry and grape anthocyanins on the growth of certain bacteria. Food Research 25, 26±32.

Sanchez-Patan, F., Bartolome, B., Martin-Alvarez, P. J., Anderson, M., Howell, A., and Monagas, M. (2012) Comprehensive assessment of the quality of commercial cranberry products. Phenolic characterization and in vitro bioactivity, J Agric Food Chem 60, 3396-3408, Shigemura K, Tanaka K, Okada H, Nakano Y, Kinoshita S, Gotoh A, Arakawa S, Fujisawa M. Pathogen occurrence and antimicrobial susceptibility of urinary tract infection cases during a 20-year period (1983-2002) at a single institution in Japan. Jpn J Infect Dis. 2005 October; 58(5):303-8.

US2010/028468;
WO2010/121203;
WO96/30033

The invention claimed is:

1. A dry cranberry extract, comprising:
    10 to 20% by weight of proanthocyanidins (PACs) in relation to the total weight of the dry extract (measured by the BL-DMAC method),
    2 to 12% by weight of organic acids in relation to the total weight of the dry extract, including:
        1-10% by weight of quinic acid in relation to the total weight of the dry extract,
        0.5-8% by weight of phenolic acids in relation to the total weight of the dry extract,
    at least 0.5% by weight of anthocyans and/or anthocyanidins in relation to the total weight of the dry extract,
    1-10% by weight of sugars in relation to the total weight of the dry extract,
    1-10% by weight of flavonols, in glycosylated/or aglycone form,
    wherein the dry cranberry extract is provided in tablet or capsule form.

2. The extract according to claim 1 wherein the polymers of PACs having a degree of polymerization greater than or equal to 4 represent at least 30% by weight, in relation to weight of all PACs present in the extract.

3. A process for preparing an extract according to claim 1, comprising the following steps:
    a) Enriching a water-soluble fraction of cranberry in non-polar polyphenolic compounds, and in organic acids, to obtain fraction I,
    b) Enriching a water-insoluble fraction of cranberry in polymers of PACs, to obtain fraction II,
    c) Combining fractions I and II obtained in steps a) and b), respectively, in proportions corresponding to a weight ratio (fraction I/fraction II) ranging between 30/70 and 70/30, and
    d) Enzymatic digestion with at least one esterase wherein the esterase is a tannase, a cinnamoyl-esterase, or a β-glucosidase or a mixture thereof.

4. The process according to claim 3, wherein:
    the water-soluble fraction used in step a) is cranberry juice and the water-insoluble fraction used in step b) is cranberry marc, or
    The water-soluble fraction used in step a) and the water-insoluble fraction used in step b) were obtained from whole cranberries, by:
        i) Crushing whole cranberries, and
        ii) Decanting and separating the water-soluble and water-insoluble fractions.

5. The process according to claim 3 wherein fraction I is obtained in step a) by the following steps:
    a1) separating non-polar compounds and polar compounds by:
        adsorption of the water-soluble fraction on a non-polar support,
        washing with a polar solvent and collecting polar fraction Ia, and
        eluting and collecting non-polar fraction Ib;

a2) separating organic acids and sugars present in polar fraction Ia by:
  adsorption of fraction Ia on ion-exchange resin,
  washing with aqueous solvent,
  eluting with acidic solvent and collecting fraction Ic comprising organic acids;
a3) Combining fractions Ib and Ic to form fraction I.

6. The process according to claim 3 wherein fraction II is obtained in step b) by treatment comprising a step of extracting polymers of PACs from the water-insoluble fraction with organic solvent.

7. The process according to claim 3, wherein the combining of fraction I obtained in step a) and fraction II obtained in step b) is carried out by simple mixing of fractions I and II, without removing part of one of the fractions.

8. The process according to claim 3 wherein step d) of enzymatic digestion with at least one esterase is carried out:
  before step a), either during preparation of the water-soluble and water-insoluble fractions on crushed material, or on the water-soluble fraction and the water-insoluble fraction,
  between steps a) and b) and final combination step c), on fractions I and II, or
  at the end of the process, on the combined extract obtained at the conclusion of step c).

9. An extract obtainable by the process according to claim 3.

10. A food or nutraceutical composition, comprising an extract according to claim 1.

11. A pharmaceutical composition, comprising an extract according to claim 1.

12. A method for the prevention or treatment of urinary tract infections comprising administering to a subject an effective quantity of the extract of claim 1.

13. A food or nutraceutical composition comprising an extract according to claim 9.

14. A pharmaceutical composition comprising an extract according to claim 9.

15. A method for the prevention or treatment of urinary tract infections comprising administering to a subject an effective quantity of the extract of claim 9.

16. The cranberry extract of claim 1 wherein the cranberry extract is a de-esterified cranberry extract.

* * * * *